United States Patent [19]
Landolt

[11] Patent Number: 6,083,498
[45] Date of Patent: Jul. 4, 2000

[54] CHEMICAL ATTRACTANTS FOR YELLOWJACKETS AND PAPER WASPS

[75] Inventor: Peter J. Landolt, Yakima, Wash.

[73] Assignee: The United States of America as represented by the Secretary of Agriculture, Washington, D.C.

[21] Appl. No.: 09/041,056

[22] Filed: Mar. 10, 1998

[51] Int. Cl.[7] .......................... A01N 25/00; A01N 25/18; C12P 7/54
[52] U.S. Cl. .......................... 424/84; 424/403; 424/405; 514/566; 514/552; 514/744; 536/69; 536/70
[58] Field of Search .......................... 536/69, 70; 562/523, 562/531, 536, 548; 560/1; 502/512; 435/140; 264/37.22; 203/16, 409; 424/405, 403, 84; 514/560, 552, 744, 724

[56] References Cited

U.S. PATENT DOCUMENTS

| | | | |
|---|---|---|---|
| 3,485,868 | 12/1969 | Eddy et al. | 260/488 |
| 3,608,085 | 9/1971 | Papworth | 424/317 |
| 3,803,753 | 4/1974 | Feigin et al. | 119/131 |
| 3,912,810 | 10/1975 | Eddy et al. | 424/84 |
| 4,278,715 | 7/1981 | Romero-Sierra et al. | 428/22 |
| 4,360,987 | 11/1982 | Lowder | 43/122 |
| 4,851,218 | 7/1989 | Hildebrandt et al. | 424/84 |
| 5,229,126 | 7/1993 | Anderson et al. | 424/410 |
| 5,556,881 | 9/1996 | Marisi | 514/557 |
| 5,557,880 | 9/1996 | Schneidmiller | 43/122 |
| 5,662,914 | 9/1997 | Shorey et al. | 424/405 |

OTHER PUBLICATIONS

R.G. Buttery, L.C. Ling, R. Teranishi and T.R. Mon, "Insect Attractants: Volatiles of Hydrolyzed Protein Insect Baits," *J. Agric. Food Chem.* 31:689–695 (1983).

H.G. Davis, G.W. Eddy, T.P. McGovern & M. Beroza, "2,4–Hexadienyl Butyrate and Related Compounds Highly Attractive to Yellow Jackets (Vespula SPP.)," *Journal of Med. Entomology* 4:275–280 (1967).

H.G. Davis, G.W. Eddy, T.P. McGovern & M. Beroza, "Heptyl Butyrate, A New Synthetic Attractant for Yellow Jackets," *Journal of Economic Entomology* 62:1245 (1969).

H.G. Davis, T.P. McGovern, G.W. Eddy, T.E. Nelson, K.M. Bertun, M. Beroza, & J.C. Ingangi, "New Chemical Attractants for Yellow Jackets (Vespula spp.)," *Journal of Economic Entomology* 61: 459–462 (1968).

H.G. Davis, R.W. Zwick, W.M. Rogoff, T.P. McGovern, & M. Beroza, "Perimeter Traps Baited with Synthetic Lures for Suppression of Yellowjackets in Fruit Orchards," *Environmental Entomology* 2:569–571 (1973).

H.G. Davis, R.J. Peterson, W.M. Rogoff, T.P. McGovern, & Beroza, "Octyl Butyrate, an Effective Attractant for the Yellowjacket," *Enviromental Entomology* 1:673–674 (1972).

T.P. McGovern, H.G. Davis, M. Beroza, J.C. Ingangi, & G.W. Eddy, "Esters Highly Attractive to Vespula spp.," *Journal of Economic Entomology* 63:1534–1536 (1970).

J.F. MacDonald, R.D. Akre, & W.B. Hill, "Attraction of Yellowjackets (Vespula spp.) To Heptyl Butyrate in Washington State (Hymenoptera: Vespidae),"*Environmental Entomology* 2:375–379 (1973).

(List continued on next page.)

*Primary Examiner*—Jose' G. Dees
*Attorney, Agent, or Firm*—M. Howard Silverstein; John D. Fado; Margaret A. Connor

[57] ABSTRACT

Compositions and lures are described which provide vapor blends of acetic acid and one or more compounds selected from the group consisting of isobutanol, racemic 2-methyl-1-butanol, S-(–)-2-methyl-1-butanol, 2-methyl-2-propanol, heptyl butyrate, and butyl butyrate which function as highly effective attractants for yellowjacket wasps and paper wasps. By attracting wasps to traps or baits, the chemical attractants provide a means for detecting, surveying, monitoring, and controlling the wasps.

18 Claims, 4 Drawing Sheets

OTHER PUBLICATIONS

R.H. Grothaus, H.G. Davis, W.M. Rogoff, J.A. Fluno, & J.M. Hirst, "Baits and Attractants for East Coast Yellow-jackets, Vespul spp.," *Environmental Entomology* 2:717–718 (1983).

J.O. Howell, T.P. McGovern, & M. Beroza, "Attractiveness of Synthetic Compounds to Some Eastern Vespula Species," *Journal of Economic Entomology* 67:629–630 (1974).

R.E. Wagner & D.A. Reierson, "Yellow Jacket Control by Baiting. 1. Influence of Toxicants and Attractants on Bait Acceptance," *Journal of Economic Entomology* 62:1192–1197 (1969).

P.D. Greany, J.H. Tumlinson, D.L. Chambers & G.M. Boush, "Chemically Mediated Host Finding by Biosteres (Opius) Longicaudatus, A Parasitoid of Tephritid Fruit Fly Larvae," *Journal of Chem. Ecol.* 3:289–195 (1977).

CHEMICAL ATTRACTANTS FOR YELLOWJACKETS AND PAPER WASPS

BACKGROUND OF THE INVENTION

1. Field of the Invention

The present invention relates to synthetic insect attractants. More particularly, the invention relates to chemical attractants and use thereof to detect, survey, monitor, and/or control yellowjackets and paper wasps.

2. Description of the Art

Yellowjackets. A number of species of yellowjackets (genera: Vespula and Dolichovespula) are pestiferous, particularly those in the Paravespula subgenus. All yellowjackets can be a stinging hazard particularly in defense of their colonies, but species in this group also scavenge for sugar-rich materials and animal carrion, bringing them into frequent contact with people when foraging away from the nest. *Vespula pensylvanica*, the western yellowjacket, is the most abundant and pestiferous native species in western North America. *Vespula germanica*, the german yellowjacket, is a major palearctic pest and has been accidentally introduced into a number of other geographic areas, including North America, South America, Australia, and New Zealand.

Efforts to control wasp populations have focused on destruction of nests or on removal of foraging workers with poison baits or traps baited with chemical attractants or food materials. The development of yellowjacket control methods based on trapping of foragers or on the killing of colonies by the use of poisoned baits has been hampered by a lack of effective attractants for most of the more pestiferous species.

Those species of yellowjackets which scavenge for food may be attracted to both meat-based and sugar-based baits. Combinations of pesticides and meats have been used to control the western yellowjacket, *Vespula pensylvanica* (Saussure) (Grant et al., *Journal of Economic Entomology* 61:1653–6 (1968)), the common yellowjacket, *Vespula vulgaris* (L.) (Wagner and Reierson, *Journal of Economic Entomology* 62:1192–1197 (1969)), and the German yellowjacket *Vespula germanica* (Fab.) (Perrott, *New Zealand Journal of Zoology* 2: 491–508 (1975); Spurr et al., *Proc. 49th New Zealand Plant Prot. Conf.* 1996: 132–136). Yellowjackets are also attracted to sweet materials, which have been used with limited success in poison baits (Edwards, *Proc. 8th Internat. Congr. IUSSL.* 300 (1977); Edwards, *Social Wasps, their Biology and Control*, 398 pages (1980); Christie, *Pest Control*, pages 30–32 (1992); Dymock et al., *Proceedings of the New Zealand Weed and Pest Control Conference* 44:38–41 (1991)). Such sweet baits have not been used extensively, in part due to their attractiveness to honey bees (Spurr, *New Zealand Journal of Zoology* 23:315–324 (1996)). The effectiveness of these baits also varies with geographical locations (Spurr, 1996, supra). Meat-based baits are also not used extensively, because of their relative expense and the short length of time that they are attractive (Spurr, *New Zealand Journal of Zoology* 22:81–289 (1995)). Synthetic food attractants added to an inert matrix may constitute a useful bait with a long field life (Ross et al., *Journal of Economic Entomology* 77:637–642 (1984), Spurr, *New Zealand Journal of Zoology* 22:81–289 (1995)).

Chemical attractants are known for some species of yellowjackets. U.S. Pat. No. 3,912,810 to Eddy et al. reports a method of attracting yellowjacket wasps (Vespula spp.) using an ester having an alcohol moiety and an acid moiety and having a chain length of from 10 to 12 carbon atoms, the alcohol moiety being derived from a saturated aliphatic hydrocarbon alcohol containing from five to six carbon atoms and the acid moiety being derived from an acid selected from the group consisting of alkenoic and alkynoic acids each containing from four to seven carbon atoms. Davis et al., *J. Med. Entomol.* 4:275–280 (1967) discovered attraction of *V. pensylvanica* to 2,4-hexadienyl butyrate, 2,4-hexadienyl propionate, and 2,4-hexadienyl isobutyrate. Subsequent tests revealed the superior attractiveness of heptyl butyrate (Davis et al., *Journal of Economic Entomology* 62:1245 (1969) and Davis et al., *Environmental Entomology* 2:569–571 (1973)) and of octyl butyrate (Davis et al., *Environmental Entomology* 1:673 (1972) and McGovern et al., *Journal of Economic Entomology* 63:1534–1536 (1970)) to *V. pensylvanica*. MacDonald et al., *Environmental Entomology* 2:375–379 (1973) reported the trapping of large numbers of queens and workers of *Vespula atropilosa* (Sladen) in addition to workers of *V. pensylvanica*, using heptyl butyrate as an attractant. These and other compounds are apparently weakly attractive or are ineffective in attracting other yellowjacket species, including the pestiferous *V. germanica, V. vulgaris, Vespula maculifrons* (Byssson) and *Vespula squamosa* (Drury) (Grothaus et al., *Environmental Entomology* 2:717–718 (1973); Howell et al., *Journal of Economic Entomology* 67:629–630 (1974); MacDonald et al., 1973, supra). U.S. Pat. No. 3,803,753 describes a method for controlling yellowjackets using a bait comprising fish-flavored food containing dodecachlorooctahydro-1,3,4-metheno-2H-cyclobuta [cd] pentalene in combination with a yellowjacket attractant consisting of heptyl butyrate. U.S. Pat. No. 4,851,218 describes a method for controlling insects of the family Vespidae utilizing interspecific insecticidal bait: (Z)-9-tricosene, (Z)-9-heneicosene and the saturated hydrocarbons tricosane and tridecane, which act as kairomones for the family Vespidae to locate its prey, the house fly, are incorporated as attractants in a proteinaceous matrix having a delayed toxicant.

Paper Wasps. Social wasps in the genus Polistes are common throughout temperate, subtropical, and tropical land areas of the world. In North America they are usually referred to as paper wasps. Some species are recognized as important predators of lepidopterous larvae and, as such, potential biological control agents of insect pests in agro-ecosystems (Gillaspy, In: Vinson S. B. 9ed., *Economic Impact and Control of Social Insects*, Praeger Press, pages 332–351 (1986); Gould and Jeanne, *Environmental Entomology* 13:150–156 (1984)). Paper wasps are often a problem insect for people because of their propensity to sting in self defense or in defense of the colony. Introductions of species of paper wasps into new areas, such as *Polistes gallicus* and *Polistes dominulus* into North America (Hathoway, *Psyche* 88:169–173 (1981); Staines and Smith, *Proc. Entomol. Soc. Wash.* 97:981 (1995); Judd and Carpenter, *Great Lakes Entomol.* 29:45–46 (1996)) and *Polistes chinensis* into New Zealand (Clapperton and Dymock, *New Zealand Journal of Zoology* 24:9–15 (1997)) are troublesome due in part to abnormally dense population levels. Paper wasps have also been a problem at towers and other tall structures in Florida, where reproductives swarm in late autumn and gynes may overwinter (Reed and Landolt, *Ann. Entomol. Soc. Amer.* 84:628–635 (1991)). There are no baits, traps, or chemical attractants used for Polistes paper wasps. Such methods may be useful in programs to detect introduced species or to manage populations where they are a problem.

The golden paper wasp, *Polistes fuscatus aurifer*, is broadly distributed throughout the northwestern United States and is a member of a complex of species and subspecies that are common and broadly distributed throughout the western hemisphere. It has accidentally been introduced into Hawaii.

SUMMARY OF THE INVENTION

The present invention is directed to attracting yellowjacket wasps and paper wasps using chemicals which provide vapor blends or vapor mixtures of (I) acetic acid and (II) one or more compounds selected from the group consisting of isobutanol, racemic 2-methyl-1-butanol, S-(–)-2-methyl-1-butanol, 2-methyl-2-propanol, heptyl butyrate, and butyl butyrate. The volatilized blends or mixtures function as highly effective attractants for yellowjacket wasps and paper wasps, and provide a means for detecting, surveying, monitoring, and controlling the wasps.

In one embodiment, the volatilized blend is provided by a mixture of I and II. In another embodiment, the vapor blend is provided by a combination of I and II wherein I and II are positioned in sufficient proximity to one another to form a volatilized blend. In still a further embodiment, the vapor blend is provided by a single chemical, e.g., 2-methylpropyl acetate (isobutyl acetate) which releases a vapor blend of acetic acid and isobutanol into the atmosphere.

This blend of the vapors of (I) acetic acid and (II) a compound selected from the group consisting of isobutanol, racemic 2-methyl-1-butanol, S-(–)-2-methyl-1-butanol, 2-methyl-2-propanol, heptyl butyrate, and butyl butyrate, yields specific attractants for yellowjackets and paper wasps, and provides a means for detecting, surveying, monitoring, and controlling these pests.

The attractants of the invention are the first known chemical attractants that work for the introduced pest species of yellowjacket wasps, *Vespula germanica*, which is now found throughout much of the United States, Europe, New Zealand, Australia, Chile, and Argentina. Further, the attractant of the invention which comprises the vapor blend of acetic acid and heptyl butyrate, is superior to the attractant in commercial use (heptyl butyrate) for *V. pensylvanica*, the principal pest species in the western United States, that is, addition of acetic acid potentiates or enhances the attractancy of heptyl butyrate.

Additionally, the invention attractants are the first chemical attractants that work for paper wasps, e.g., *Polistes fuscatus*, and provides a means for detecting, surveying, monitoring, and controlling this pest.

Without being bound by theory, it is believed that the wasp orientation to sweet food materials is the basis for their response to the attractant blend of the invention, thus foraging wasps are likely to be lured by the attractants of the invention. In use, an effective attractant amount of the vapor blend of I and II is provided in an area where wasps are to be attracted, that is, an area frequented by yellowjackets and paper wasps; an area where yellowjackets and paper wasps may forage for food or otherwise occur; or selected areas where detecting, surveying, monitoring, and/or controlling of these pests is desired. Conveniently, I and II are dispensed within a trapping means to attract and trap the wasps.

The chemical attractants of the invention are superior to non-chemical baits, e.g., jams, sugar solutions, meats, because they provide a predictable, stable, and long lasting source of attractiveness.

The invention is also directed to lures wherein I and II are held in a dispenser means which releases I and II so as to form the attractant vapor blend.

The invention is also directed to trapping systems for trapping yellowjackets or paper wasps. Such systems include trapping means, and an effective attractant amount of the attractant combination of the invention. A preferred trap is one which has a chamber wherein vapors of I and II form a blend such that the vapor blend of I and II exits the trap chamber and attracts wasps to the chamber where they are trapped.

The invention is also directed to a packaged attractant and kit for attracting yellowjacket wasps or paper wasps which include components I and II.

Yellowjackets and paper wasps are hazardous to people and livestock and cause serious medical reactions including death. Wasp foraging for food brings them into close proximity to people and human foods and is directly related to their pest status. The attractants of the invention are useful to remove such foraging wasps in areas where they are encountered by people, such as parks, campgrounds, outdoor restaurants, zoos, and yards. In many orchards and vineyards these wasps interfere with manual fruit harvesting. In forests, yellowjackets are a stinging hazard and annoyance at campgrounds and firefighter camps. The chemical attractants of the invention provide a means of reducing populations of pestiferous species over defined areas by mass trapping and alleviate threats to human and animal health. Further, when used in combination with a control agent for the wasps, such as a drowning solution, a pesticide or biological control agent, the composition can be used as a direct control agent.

The attractants of the invention can also be used as a poisoned bait by combining them with feeding stimulants and toxicants that the wasps will take back to the nest and feed to the brood and queen, effectively killing off the colony.

In sum, the novel chemical attractants of the invention provide a tool for the detection of yellowjackets and paper wasps and provide a means for population control and population density estimation of these pests. The lures and trapping systems which include the attractants of the invention are useful for homeowners, orchardists, park and recreation departments, zoos and gardens, and other users where control of yellowjackets or paper wasps is desired.

The utility and effectiveness of the invention in attracting yellowjackets and paper wasps suggests the following economic applications: (1) the detection of populations, (2) the detection of outbreaks or rapid population buildups, (3) the monitoring of populations, (4) the control of problem populations in discrete areas. In certain geographic areas there is a need to detect the presence of yellowjackets and paper wasps as they move into new areas, so that these populations may be destroyed. Yellowjackets are prone to intermittent population outbreaks in some geographic areas, causing severe problems for humans and livestock. Such outbreaks can be detected by programs to attract and trap wasps, thereby gaining information on changes in wasp numbers. The attractants of the invention are also useful as a bait for traps used to monitor changes in population level. For example, efficacy of control procedures such as colony destruction, pesticide sprays, or poison baits may be measured with attractant traps that indicate population levels. The attractants are also useful to control wasp populations and activities where they are a problem through a variety of approaches, including localized trapping out of foragers and the use of the attractant in a poison bait formulation to kill foragers and wasp colonies.

In accordance with this discovery, it is an object of the invention to provide chemical attractants for yellowjackets and paper wasps.

Another object of the invention is the provision of the attractants as detection, surveying, monitoring, or control agents for wasps.

A further object of the invention is the provision of the attractants of the invention for use with control agents, including drowning solutions, insecticides, biological control agents, or other toxicants, to attract and combat this pest.

Another object of the invention is the provision of effective methods of monitoring or controlling yellowjackets or paper wasps using the chemical attractants of the invention.

A further object of the invention is the provision of trapping systems for trapping yellowjackets or paper wasps which include trapping means and an effective attractant amount of the attractant combination of the invention.

A still further object of the invention is the provision of kits which include the components required to produce the attractant blend.

Other objects and advantages of the invention will become readily apparent from the ensuing description.

BRIEF DESCRIPTION OF THE DRAWINGS

FIG. 3 shows the percentages of female *P. fuscatus aunifer* captured in traps baited with a 0.5% concentration of acetic acid in the drowning solution and different dosages of isobutanol, formulated as 1 ml of different percentages of isobutanol in mineral oil in caps.

DETAILED DESCRIPTION OF THE INVENTION

This invention comprises specific attractants for yellowjackets and paper wasps, and provides a means for detecting, surveying, monitoring, and controlling these pests. The synthetic attractant composition of the invention comprises a vapor blend or vapor mixture of vapor of (I) acetic acid and vapor of (II) one or more compounds selected from the group consisting of isobutanol, racemic 2-methyl-1-butanol, S-(−)-2-methyl-1-butanol, 2-methyl-2-propanol, heptyl butyrate, and butyl butyrate, in an effective attractant amount. Attracted wasps respond to the combination of odorants from I and II present simultaneously in air and they move upwind towards the source of the blend. An effective amount of an attractant vapor blend of I and II is defined as that quantity of the chemical blend that attracts yellowjackets or paper wasps to the location of the blend at a rate higher than wasps are attracted to a location devoid of the blend. An effective attractant amount is determined as the quantities of the compounds emitted from a formulation or dispenser holding the compounds that is sufficient to elicit attraction response from wasps downwind of the attractant vapor blend or mixture.

The attractant vapor composition may be provided by (a) a mixture of I and II; (b) a combination of I and II wherein I and II are positioned in sufficient proximity to each other effective to form a volatilized blend of I and II; or (c) a single compound, e.g., 2-methylpropyl acetate, which dissociates into a vapor blend of I and II, e.g., a vapor blend of acetic acid and isobutanol. In all cases, whether I and II are formulated or presented separately or together, I and II are provided so as to provide an effective attractant amount of the odor blend of I and II.

All of the compounds for producing the vapor composition of the invention are commercially available. Acetic acid vapor is provided by compounds that produce volatilized acetic acid, for example, aqueous acetic acid, glacial (concentrated) acetic acid or ammonium acetate. Component II vapor is provided by compounds isobutanol, racemic 2-methyl-1-butanol, S-(−)-2-methyl-1-butanol, 2-methyl-2-propanol, heptyl butyrate, and butyl butyrate to the mixture. A vapor blend of acetic acid and isobutanol may be also provided by 2-methylpropyl acetate which dissociates to form a volatilized blend of acetic acid and isobutanol. All of the foregoing compounds except 2-methyl-2-propanol (melting point of 25° C.) are liquid over the range of temperature at which wasps actively forage in nature, which is about 5 to 35° C., with most activity of concern occurring from about 15 to 30° C.

Lures. It is envisioned that the chemical attractants of the invention would be useful in detecting, surveying, monitoring, or controlling yellowjackets and/or paper wasps or wasp populations when used as a lure. A lure includes a dispenser means which contains a chemical or chemicals which provide the attractant vapor blend. For purposes of this invention, a dispenser means is defined as any means which both (a) contains or holds the unvolatilized compound or compounds used to produce the vapor blend of I and II and (a) releases the compound or compounds in the vapor phase to form the vapor blend of I and II.

A dispensing means may take several forms. For example, it may be as simple as a fencepost or tree, wherein a formulation to produce volatilized I and II is painted, sprayed, or otherwise applied to the fencepost or tree, for release into the ambient area. Other dispensing means include an adsorbent material such as cotton or paper which both holds and releases I or II. In general, however, a dispensing means will comprise a reservoir for holding an amount of a compound either within a space or a polymeric matrix, with the release into the atmosphere controlled by a permeable wall or membrane or by a small opening surrounded by an impermeable wall or membrane. Examples of dispensers include a reservoir and polyethylene cap within a trap as described Examples 1–3, below. Further examples of dispensers include polymer caps, bubbles, hollow fibers, hollow tubes or tubing which release compounds through the walls, capillary tubing which release compounds out of an opening in the tubing, polymeric blocks of different shapes which release compounds out of the polymer matrix, membrane systems which hold the chemicals within an impermeable container and release them through a measured permeable membrane, and combinations of the foregoing. Examples of other dispensing means are polymer laminates, polyvinyl chloride pellets, microcapillaries, and Shunitzu rope. Another dispensing means includes using microencapsulation techniques to encapsulate each compound used to produce the vapor blend.

In one embodiment, I and II are formulated as a mixture and placed in the dispensing means. In another embodiment, the compound that produces acetic acid vapor is provided in a first dispenser and the compound or compounds that produce vapor of component II is placed in a second dispenser, and the two dispensers are placed in sufficient proximity to one another to form a volatilized blend of I and II in the surrounding atmosphere. The first and second dispensers may optionally be attached or fused to form one device or unit that releases I and II to form the vapor blend. Alternatively, I and II may be for formulated seperately, for example, placing acetic acid in a drowning solution and placing a compound of group II in a polyethylene cap as described in Example 1–3, below. In still another embodiment, the vapor blend of I and II is provided by 2-methylpropyl acetate which releases acetic acid and isobutanol vapors as a blend.

Effective odorant amounts (I and II released individually as a vapors into air) are most readily defined as weight amounts released per unit time from a formulation, dispenser, bait or trap. The broad range of release rates is that which is an effective attractant for the target yellowjacket or paper wasp. An effective release rate range of acetic acid is at least about 10 $\mu$g per hour. A preferred release rate range for acetic acid is from about 50 $\mu$g per hour to 1000 $\mu$g per hour. An effective release range for compound of II is at least about 40 $\mu$g per hour except at least about 5 $\mu$g per hour for 2-methyl-2-propanol. A preferred release rate range for isobutanol (2-methyl-1-propanol) is about 50 $\mu$g per hour to 200 $\mu$g per hour. A preferred release rate range for racemic 2-methyl-1-butanol or S-(−)-2-methyl-1-butanol is about 40 $\mu$g per hour to 500 $\mu$g per hour. A preferred release rate range for 2-methyl-2-propanol is about 10 $\mu$g per hour to 200 $\mu$g per hour. A preferred release rate range for heptyl butyrate or butyl butyrate is about 100 $\mu$g per hour to 500 $\mu$g per hour.

Controlled release of the compounds may also be effected in part through the addition of an extender such as mineral oil, which will reduce the rate of volatilization of the odorants out of the dispenser.

Factors such as wasp species present, wasp population density, and environmental factors influencing wasp foraging behavior (e.g., temperature, wind velocity, rain, time of day and seasonality) will influence the response of wasps to the attractants of the invention and the actual number of wasps attracted. The amounts of I and II in a particular set of circumstances that will provide release rates within an effective range can be readily determined by dose response field tests as described in Examples 1 and 3, below.

The lures may be combined with feeding stimulants to provide baits for yellowjackets and paper wasps. Toxicants may also be added to provide poisoned baits, as discussed in detail below. Other compounds and materials may be added to a formulation, lure, bait or trap provided they do not substantially interfere with the attractancy of the attractant vapor composition of the invention. Whether or not an additive substantially interferes with the attractant activity can be determined by standard test formats, involving direct comparisons of efficacy of the blend without an added compound and the blend with an added compound. Reductions in attractancy, such as reduced captures of wasps in traps baited with the attractant with the additive, may be determined with standard statistical analyses.

Trapping Systems. The attractants of the invention may be used as detecting agents, surveying agents, monitoring agents, or control agents for the yellowjackets or paper wasps. Conveniently, the attractants are dispensed within a trapping means to attract and trap wasps. A trapping system for monitoring or controlling yellowjacket wasps or paper wasps includes a trapping means, and a dispenser means located within the trapping means which provides an effective attractant amount of a vapor blend of vapor of (I) acetic acid and vapor of (II) one or more compounds selected from the group consisting of isobutanol, racemic 2-methyl-1-butanol, S-(−)-2-methyl-1-butanol, 2-methyl-2-propanol, heptyl butyrate, and butyl butyrate. A trapping means is any device for catching insects, particularly, yellowjackets and paper wasps. These include for example, the yellow jacket trap described in U.S. Pat. Nos. 5,557,880; 5,522,172; 5,501,033; 5,339,563; 4,858,374; 4,794,724; 4,551,941; 4,348,449; 4,179,252; 4,064,206; and 3,803,753 which are incorporated herein by reference. Other traps included the Trappit dome trap by Agrisense, Final Flight® Yellowjacket wasp trap by Troy Bioscience (Phoenix, Ariz.), Liquidator Trap by Phero Tech Inc., Yellow Jacket Wasp Trap by Oak Stump Farm (U.S. Pat. No. 4,794,724), and Rescue® Yellowjacket Trap by Sterling (U.S. Pat. No. 4,551,941).

A preferred trap is one which has a mixing chamber wherein vapors of I and II form a blend and the vapor blend of I and II exits the trap chamber and attracts wasps to the chamber where they are trapped. Compounds I and II that produce the attractant vapor blend may be presented as a mixture or in separate dispensers within the trap. Acetic acid and a compound of II, for example, alcohol compounds, may be added directly to a drowning solution that can be used in a trap, with the attractant blend emanating from the drowning solution. This drowning solution may optionally contain additional materials that aid in the capture and killing of attracted wasps, such as detergents or wetting agents, clays, dyes and toxicant, as long as such additives do not substantially interfere with the attractiveness of the attractant blend of the invention.

For dry traps, in which attracted wasps are killed by toxicant or insolation, other formulation methods may be used as known in the art.

Means for Controlling Wasps. The attractants of the invention are useful for control of yellowjackets and paper wasps when used in concert with means for controlling wasps. Control of wasps may be carried out as known in the art, including (a) by capturing the wasps in traps, (b) by capturing wasps in a trap and killing the wasps, for example, by means of a drowning solution or pesticide for yellowjackets and paper wasps, or (c) by use of toxicants, pesticides or chemosterilants, (d) by use of poisoned bait, e.g., the combination of a feeding stimulant and toxicant, that the wasps will take back to the nest and feed to the brood and queen, effectively killing off the colony, or (e) by use of pathogens, for example, by bringing the attracted wasps into contact with pathogens or by incorporating pathogens into the baits for dissemination throughout the nest.

Insecticides or toxicants for yellow jackets include compounds such as dimethyl (2,2,2-trichloro-1-hydroxyethyl) phosphonate, 2,2-dichlorovinyl dimethyl phosphate, and 1,2-dibromo-2,2-dichloroethyl dimethyl phosphate. Other toxicants are selected from the group consisting of organophosphorus toxicants, carbamates, inorganic toxicants, and insect growth regulators. U.S. Pat. No. 4,851,218 describes toxicants for use to control wasps, which patent is incorporated herein by reference.

The use of slow acting insecticides or of chemosterilants in the attractant allows the yellowjacket to return to the nest and may provide a more effective means of controlling yellowjacket populations than trapping.

A toxicant may be in a powdered form or incorporated into a bait whereby the wasp becomes attracted to the toxicant and becomes contaminated or infected (in the case of pathogens) with the toxicant or carries the toxicant back to the nest where it is spread throughout the nest and eradicates the members of the colony. Toxicants which may be useful in this invention are those which will not adversely affect the attractiveness of the attractants of the invention. A variety of matrix materials may also be employed as a carrier for the toxicant.

Combination of attractant and visual target. For purposes of trapping or baiting, visual targets may be used to focus close range orientation of attracted wasps, either to facilitate their being captured in traps or to facilitate their arrival on a bait. For example, some species of yellowjackets are optimally attracted to the color yellow, and some species are attracted to small dark objects which they will contact.

Kits and packaged attractants. The invention is also directed to kits. In one aspect the kit includes a trap and a lure for use within the trap and which provides the attractant vapor blend. The kit may also include a drowning solution for some trap designs. Another kit includes two components, wherein one component is acetic acid and the other component is one or more compounds selected from the group consisting of isobutanol, racemic 2-methyl-1-butanol, S-(–)-2-methyl-1-butanol, 2-methyl-2-propanol, heptyl butyrate, and butyl butyrate and means for dispensing the compounds to provide the attractant blend of the invention. The components may be in a drowning solution, formulation (chemical matrix to hold and release one or more attractant chemicals), dispenser or bait as discussed above. Drowning solutions, formulations, dispensers and controlled release devices may be rechargeable with a measured amount of I and II.

A bait kit may contain the compounds to provide the attractant blend of the invention in a matrix or suitable carrier for wasps to contact and remove. The bait may also contain additives, such as feeding stimulants, toxicants, extenders, antioxidants, and/or UV adsorbers.

The invention is also directed to a packaged attractant which comprises two components, wherein one component is one that provides acetic acid vapor and the other component is one or more compounds selected from the group consisting of isobutanol, racemic 2-methyl-1-butanol, S-(–)-2-methyl-1-butanol, 2-methyl-2-propanol, heptyl butyrate, and butyl butyrate, wherein the components are packaged in separate containers and wherein the packaged attractant further comprises instructions for producing a volatilized blend of the two components when the components are released from the containers.

USES OF THE INVENTION

The chemical attractant is useful in detecting, surveying, monitoring, or controlling wasp populations, including Vespula spp., Dolichovespula spp., Vespa spp., and Polistes spp. Examples include *Vespula germanica* (the German wasp), *Vespula pensylvanica* (the western yellowjacket), *Vespula vulgaris* (the common wasp), *Vespula maculifrons* (the eastern yellowjacket), *Vespula squamosa* (the southern yellowjacket), *Dolichovespula arenaria* (the aerial yellowjacket), *Dolichovespula maculata* (bald faced hornet), *Vespa crabro* (the European hornet), *Polistes fuscatus aunifer* (golden paper wasp), *Polistes dominulus*, and *Polistes gallicus*.

When used as a detection, survey, or monitoring agent, traps are baited with the novel attractant of the invention and the catch tabulated to determine size and location of infestation. Economic use of appropriate control agents can then be determined.

As discussed above, use of the attractants as control agents can be carried out in several ways. The attractant may be placed within a trap which allows the insects to enter but prevents their exit. In this manner, the foraging power of the colony is reduced thereby achieving some degree of control over the colony. Another method is to use the attractant to attract the wasps to suitable substrates and subsequently or simultaneously expose the insects to insecticides which control the wasps. An effective amount of the insecticide, toxicant or other bioactive chemical or material is used, that is, an amount sufficient upon contact or ingestion to kill the wasp, to render it impaired sufficiently to be trapped, drowned, or insolated, or to disrupt neural or other physiological functions to prevent essential colony functions or reproduction. An effective amount of a pathogen or disease organism is used, that is, an amount sufficient upon contact or ingestion or carried by the wasp, to kill the wasp or to be carried back to the nest and distributed to colony members, effectively initiating an epizootic to kill the colony. Insecticides can be used in traps baited with the attractant, thereby minimizing the dissemination of the insecticide. Chemosterilants can be used in conjunction with the composition to attract and sterilize wasps, particularly queens and males.

Another method to control the wasps using the composition of the invention is to detect the location and boundaries of localized wasp populations, and then employ in the area biological control agents.

EXAMPLES

The following examples are intended only to further illustrate the invention and are not intended to limit the scope of the invention which is defined by the claims.

Example 1

The following example describes trapping experiments conducted to evaluate chemicals as attractants for species of yellowjackets present locally in Yakima County, Washington and to compare the attractiveness of these chemicals at different dosages.

Materials and Methods. The first experiment evaluated heptyl butyrate, butyl butyrate, isobutanol, and an acetic acid solution as baits for yellowjackets. Heptyl butyrate was included for comparison because of its known attractiveness to *V. pensylvanica* (Davis et al., 1969, supra). Butyl butyrate was also reported previously to be attractive to *V. pensylvanica* (McGovern et al., 1970, supra). Subsequent experiments evaluated dosages of isobutanol, dosages of heptyl butyrate, and concentrations of acetic acid in water.

Yellowjacket Trappit Dome traps (Agrisense, Fresno, Calif.) were used in all experiments. All traps contained 200 ml of a drowning solution comprised of water (200 ml), clay (20 mg), Palmolive concentrated dishwashing liquid (25 $\mu$l) (Colgate-Palmolive, N.Y., N.Y.) and Schilling food color (50 $\mu$l yellow, 25 $\mu$l blue, and 60 $\mu$l red) (McCormick & Co., Hunt Valley, Md.). Acetic acid was added to this solution in some treatments as an attractant. Heptyl butyrate, butyl butyrate, and isobutanol were formulated in 3 dram polyethylene caps (Kimbel Glass Co., Vineland, N.J., part No. 60975D-3) that were pinned to the inside top of the trap.

Trap plots were near Parker Heights, Moxee, and 15 miles east of Moxee, Yakima County, Washington. Traps were placed in fruit trees, windbreak trees, and on fencing, 1 to 1.5 m above ground and about 10 m apart.

Chemical Treatments. Six chemical treatments were selected and compared to a control as baits for yellowjackets. The principal objectives of this experiment were to determine if isobutanol with acetic acid and butyl butyrate with acetic acid are attractive to yellowjackets (*V. germanica* and *V. pensylvanica*) and to compare the attractiveness of these chemicals to that of heptyl butyrate, a known chemical attractant for western yellowjackets (Davis et al. 1969). Treatments were: (1) one ml of heptyl butyrate, (2) one ml of heptyl butyrate and 0.5% acetic acid in the 200 ml of drowning solution, (3) one ml of butyl butyrate, (4) one ml of butyl butyrate and 0.5% acetic acid in the 200 ml of drowning solution, (5) one ml of isobutanol, and (6) one ml of isobutanol and 0.5% acetic acid in 200 ml of drowning solution. The control trap contained 200 ml of the drowning solution without acetic acid. A randomized complete block design was used with each treatment represented per block and 10 blocks set up in 3 widely separated (8 to 20 km) orchards. This experiment was begun on Jul. 26, 1997. Traps were checked 3 times per week. Wasps were removed and counted and the drowning solution in the trap (with or without acetic acid) was augmented or replaced. Wasps captured were tallied by species, sex, and caste. This experiment was maintained for 2 weeks.

Data for workers of *V. atropilosa*, *V. germanica*, and *V. pensylvanica* were analyzed by analysis of variance, using data only from blocks in which >9 workers of a species were captured per block per trap check, after transformation to percents of block totals. Treatment means were separated by Tukey's Test at the 0.05 level.

Comparisons of dosages of heptyl butyrate and of isobutanol. Different dosages of heptyl butyrate were compared as an attractant for *V. pensylvanica* and different dosages of isobutanol were compared as an attractant for both *V. pensylvanica* and *V. germanica*. Those two experiments were conducted using traps also containing 0.5% acetic acid in the drowning solution.

A range of heptyl butyrate dosages (providing a range of release rates) was obtained by using a range of concentrations of heptyl butyrate in mineral oil. Caps were loaded with one ml of 0, 12.5, 25, 50, 75, and 100% heptyl butyrate (by volume) in mineral oil. A randomized complete block design was used, with 6 sets of the 6 treatments in traps placed in groves of fruit trees. Each set or block was comprised of one each of the 6 treatments. This experiment was begun Aug. 18, 1997. Traps were checked and randomized every 2 to 3 days over 10 days, providing 18 replicates (3 randomizations of 6 block replicates).

Two experiments were conducted to compare dosages of isobutanol in mineral oil as an attractant for yellowjackets. A low dose range was conducted after it was determined that the lowest dose of the high dose series was near optimum for capture of *V. germanica* in traps. For both experiments, isobutanol was combined with mineral oil and loaded into polyethylene caps. Caps were loaded with one ml of a mixture of isobutanol in mineral oil at the following percentages by volume: 0, 12.5, 25, 50, 75, and 100% for the first test, and 0, 1, 2, 4, 8, and 16% for the second test. For each test, a randomized complete block design was used, with 6 sets of treatments in traps placed in groves of fruit trees. Each set or block was comprised of one each of the 6 treatments. Traps were checked, insects were removed, and treatments were randomized every 2 to 3 days over 10 days, providing 18 replicates (3 randomizations of 6 block replicates). The high dose test was begun Aug. 8, 1997, and the low dose test was begun Aug. 26, 1997.

Trap data were transformed to percentages of block totals before analyses. Regression analyses were performed on transformed data to determine if trap catches varied significantly with dosage. Additionally, differences among treatment means were determined using analysis of variance and Tukey's test at the 0.05% level.

Comparison of concentrations of acetic acid. Two experiments were conducted to evaluate the effectiveness of different percentages of acetic acid in water, with heptyl butyrate or isobutanol in caps, as an attractant for *V. germanica* and *V. pensylvanica*. These experiments were comparisons of 0, 0.125, 0.25, 0.5, 1, and 2% acetic acid in water used to make the drowning solution, with 200 ml put into each trap. In the first experiment, all traps were also baited with a cap containing 1 ml of a 50% mixture of heptyl butyrate in mineral oil. Traps with these 6 bait treatments were set up in a randomized block design, with 6 blocks of traps set up at different locations. This experiment was begun Sep. 2, 1997. Traps were checked and insects removed every 2 to 3 days for 1 week. At each check date, treatment positions within blocks were randomized, providing 18 replicates per treatment (6 blocks times 3 trap checkings).

The above experiment was repeated in its entirety with caps loaded with isobutanol. The same concentrations of acetic acid in water were tested and all traps contained a cap loaded with 1 ml of a mixture of 16% isobutanol in mineral oil. Six blocks of traps were checked every 2 to 3 days and were randomized each time they were checked. This experiment was begun Sep. 9, 1997. These were maintained for 16 days, providing 36 replicates per treatment (6 blocks times 6 trap checkings).

Trap data were transformed to percentages of block totals before analyses. Regression analyses were performed on transformed data to determine if trap catches varied significantly with dosage. Additionally, differences among treatment means were determined using analysis of variance and Tukey's test at the 0.05 level.

All statistical procedures were conducted using the StatMost program by DataMost (*StatMost Statistical Analysis and Graphics*, DataMost Corporation, Salt Lake, Utah (1995)). All data reported are for the worker caste only.

Results.

Chemical comparisons. In the first experiment, trap catches and differences among treatments varied with yellowjacket species. Numbers of *V. germanica, V. pensylvanica,* and *V. atropilosa* workers captured were suitable for statistical comparisons.

Significant numbers of *V. germanica* were captured in traps baited with heptyl butyrate plus acetic acid, butyl butyrate plus acetic acid, and isobutanol plus acetic acid (Table 1). Isobutanol plus acetic acid was most attractive by far, while butyl butyrate plus acetic acid was more attractive than heptyl butyrate plus acetic acid. A total of 946 worker *V. germanica* were captured in this test.

Significant numbers of *V. pensylvanica* workers were captured in traps baited with heptyl butyrate, with heptyl butyrate plus acetic acid, with butyl butyrate plus acetic acid, and with isobutanol plus acetic acid (Table 1). Numbers of *V. pensylvanica* captured in traps baited with isobutanol plus acetic acid were significantly greater than those captured in traps baited with heptyl butyrate only. However, greatest captures were in traps baited with heptyl butyrate plus acetic acid. A total of 6695 worker *V. pensylvanica* were captured in this test.

Significant numbers of *V. atropilosa* were captured in traps baited with heptyl butyrate, heptyl butyrate plus acetic acid, butyl butyrate, butyl butyrate plus acetic acid, and isobutanol and acetic acid (Table 1). Heptyl butyrate and heptyl butyrate plus acetic acid were most attractive by far, with no difference in attractiveness of heptyl butyrate with or without acetic acid. A total of 556 worker *V. atropilosa* were captured in this test.

Comparisons of dosages of heptyl butyrate and of isobutanol with acetic acid. There was a positive relationship between dosages of heptyl butyrate with 0.25% acetic acid and percentages of *V. pensylvanica* captured ($r^2$=0.91, t=4.27, df=4, p=0.013), *V. germanica* captured ($r^2$=0.98, t=10.15, df=4, p=0.0005), and *V. atropilosa* captured ($r^2$=0.95, t=6.20, df=4, p=0.0035. *V. pensylvanica* captured in traps baited with heptyl butyrate were significantly greater than the control (acetic acid and no heptyl butyrate) by Tukey's test for all dosages tested (Table 2). Captures of *V. pensylvanica* in traps baited with 50%, 75%, and 100% heptyl butyrate in mineral oil were similar and were greater than captures in traps baited with 12.5% and 25% heptyl butyrate in mineral oil (Table 2). *V. germanica* captured in traps baited with the two highest dosages of heptyl butyrate tested were significantly greater the control traps. Nearly no *V. atropilosa* were captured in traps baited with acetic acid and no heptyl butyrate, while captures of this species in traps baited with the highest dosage of heptyl butyrate were significantly greater than captures in traps with all other dosages (Table 2). Totals of 8324 worker *V. pensylvanica*, 516 *V. atropilosa* and 421 *V. germanica* were captured in this test.

Figure 1:
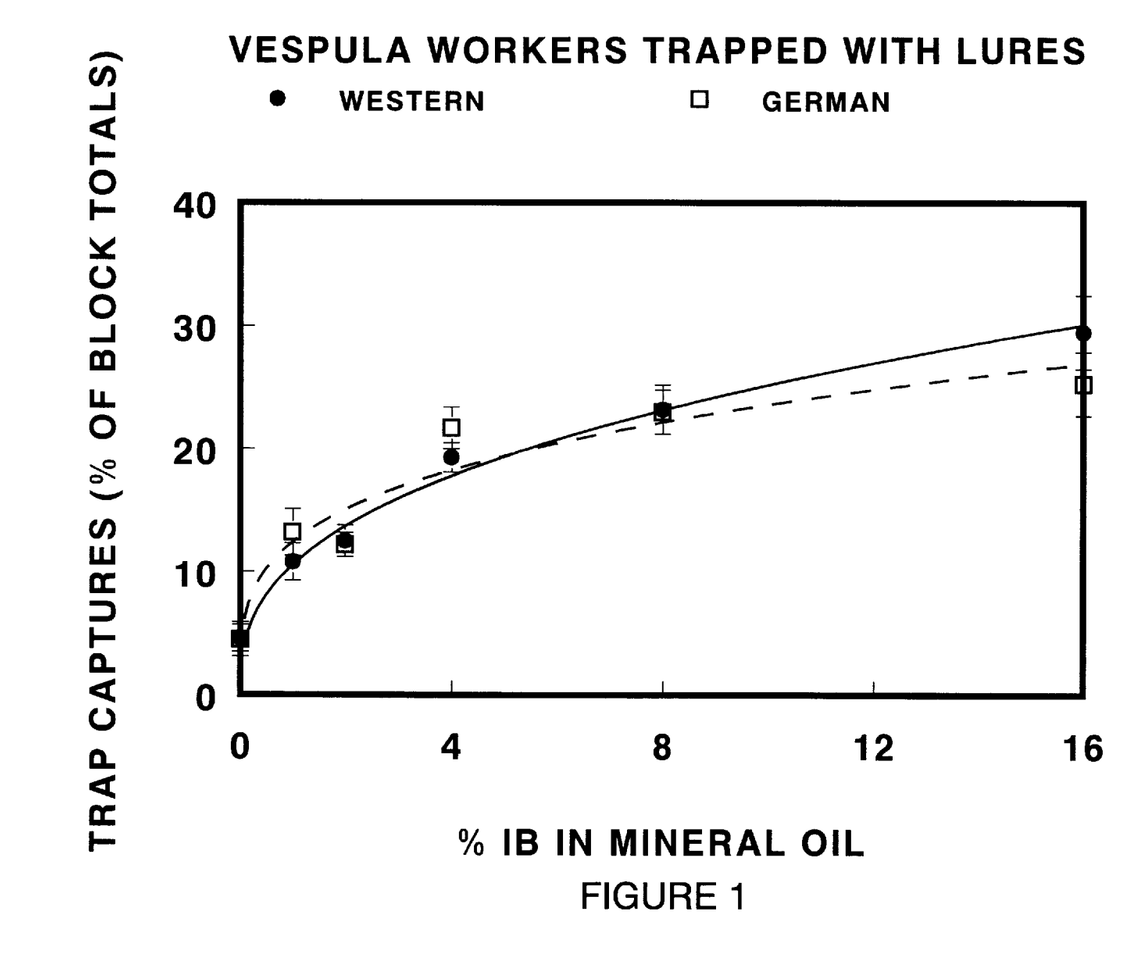
FIG. 1 shows the mean percentages (±SE) of wasps per block captured in traps baited with a 0.25% acetic acid solution and either one ml of 1%, 2%, 4%, 8%, 12% or 16% isobutanol in mineral oil. Wasps captured were *V. pensylvanica* (solid line) and *V. germanica* (dashed line) yellowjackets.

For the high dosage series of isobutanol (Table 2), a positive relationship was not demonstrated between dosages of isobutanol and captures of *V. germanica* ($r^2$=0.52, t=1.22, df=4, p=0.29) or captures of *V. pensylvanica* ($r^2$=0.69, t=1.92, df=4, p=0.13). For the low dosage series (FIG. 1), a positive relationship was demonstrated between dosages of isobutanol and captures of *V. germnanica* ($r^2$=0.82, t=2.87, df=4, p=0.046) and *V. pensylvanica* ($r^2$=0.93, t=5.17, df=4, p=0.0007). Captures of worker *V. germanica* and *V. pensylvanica* in traps baited with different amounts of isobutanol in mineral oil were significantly greater than the control for all dosages tested in both the low dose and the high dose series (Table 2, FIG. 1). By Tukey's test (ANOVA F=19.8), numbers of *V. germanica* captured were similar in the 3 highest doses tested in the low dosage series with isobutanol and captures in those doses (1 ml of 4, 8, or 16%) were all significantly greater than the three lowest doses (1 ml of 0, 1, or 2%) ($p \leq 0.05$). Percentages of *V. pensylvanica* captured in the highest dose of the low dosage series of isobutanol (16%) were significantly greater than that of all other doses (ANOVA F=24.9; Tukey's test, $p \leq 0.05$). A total of 5,015 *V. pensylvanica* and 1,168 *V. germanica* were captured in the high dose series with isobutanol, while 3,464 *V. germanica* and 4,579 *V. pensylvanica* were captured in the low dosage series with isobutanol. Numbers of *V. atropilosa* captured were not sufficient for statistical comparisons in these experiments.

Comparison of concentrations of acetic acid. When concentrations of acetic acid were tested in combination with heptyl butyrate, there was no indication that acetic acid enhanced the attraction of *V. pensylvanica* workers to heptyl butyrate (Table 3) ($r^2$=-0.69, t=1.93, df=4, p=0.13). At the highest concentration of acetic acid (2%), captures of worker *V. pensylvanica* were significantly less than in traps baited without acetic acid (0%), indicating a repellent effect. A total of 7,412 worker *V. pensylvanica* were captured in this test. Results with *V. germanica* were similar, with no significant relationship between wasps captured and acetic acid concentration ($r^2$=-0.72, t=2.08, df=4, p=0.11). Percentages of *V. gennanica* captured were significantly lower at the two highest acetic acid concentrations tested (1 and 2%), compared to all other concentrations. A total of 301 *V. germanica* were captured in this test.

When concentrations of acetic acid were tested in combination with isobutanol, there was no relationship between concentrations and captures of *V. germanica* ($r^2$=0.34, t=0.89, df=4, p=0.51) or *V. pensylvanica* ($r^2$0.41, t=0.89, df=4, p=0.42). However, significantly greater percentages of both *V. pensylvanica* and *V. germanica* workers were captured in traps baited with isobutanol and acetic acid, compared to isobutanol alone (Table 3). Although greatest captures of *V. germanica* were in traps baited with 0.5% acetic acid and isobutanol, there were no significant differences among captures of these wasps in traps baited with different concentrations of acetic acid (Tukey's test p>0.05). Similarly, there were no significant differences in captures of *V. pensylvanica* among traps baited with different concentrations of acetic acid, although all were significantly greater than captures of wasps in traps baited only with isobutanol. Totals of 4,783 *V. pensylvanica* and 8,822 *V. germanica* workers were captured in traps in this experiment. Numbers of *V. atropilosa* captured in these experiments were not sufficient for statistical comparisons.

TABLE 1

Percentages of worker yellowjackets captured in traps baited with heptyl butyrate (HB), butyl butyrate (BB), and isobutanol (IB) with and without a 0.5% acetic acid solution (AA). Percentages are based on block totals.
Means in a column followed by the same letter are not significantly different at the 0.05 level by Tukey's test.

| | Mean + SE | | |
| --- | --- | --- | --- |
| Treatment | V. germanica | V. pensylvanica | V. atropilosa |
| Control | 0 ± 0a | 0 ± 0a | 0 ± 0a |
| HB[1] | 2.9 ± 1.1a | 16.7 ± 2.3b | 42.6 ± 3.9c |
| HB + AA | 7.8 ± 1.7b | 43.4 ± 3.4d | 44.5 ± 4.5c |
| BB[1] | 4.5 ± 1.0a | 3.0 ± 0.8a | 3.8 ± 0.8b |
| BB + AA | 15.8 ± 4.0c | 14.1 ± 2.3b | 3.9 ± 0.9b |
| IB[1] | 3.4 ± 1.0a | 0.8 ± 0.3a | 0.8 ± 0.5ab |
| IB + AA | 61.2 ± 6.8d | 20.5 ± 3.1c | 4.2 ± 1.2b |

[1]Not in accordance with the invention. For comparison purposes.

TABLE 2

Mean percentages (±SE) of worker yellowjackets captured in traps baited with 0.5% acetic acid in the drowning solution and different doses of either heptyl butyrate or isobutanol in mineral oil in caps. Means in a column followed by the same letter are not significantly different by Tukey's test at p < 0.05.

|  | heptyl butyrate | | | isobutanol | |
|---|---|---|---|---|---|
| % in 1 ml | V. germanica | V. pensylvanica | V. atropilosa | V. germanica | V. pensylvanica |
| 0 | 9.0 ± 1.9a | 1.6 ± 0.4a | 0.2 ± 0.2a | 4.7 ± 0.7a | 5.9 ± 0.8a |
| 12.5 | 13.9 ± 3.2ab | 10.0 ± 0.8b | 9.1 ± 2.2b | 21.6 ± 2.7c | 15.2 ± 1.6b |
| 25 | 14.3 ± 3.3abc | 13.3 ± 1.1b | 9.1 ± 2.3b | 19.1 ± 2.3bc | 20.7 ± 2.0cd |
| 50 | 17.9 ± 3.2abc | 24.9 ± 1.8c | 24.9 ± 3.4c | 13.6 ± 2.0b | 16.9 ± 2.4bc |
| 75 | 20.5 ± 4.6bc | 24.7 ± 2.2c | 21.6 ± 2.6c | 22.9 ± 2.1c | 22.5 ± 1.9d |
| 100 | 24.3 ± 3.0c | 25.6 ± 1.6c | 35.1 ± 3.8d | 19.9 ± 2.2bc | 19.7 ± 1.3bcd |

TABLE 3

Mean percentages (±SE) of worker yellowjackets captured in traps baited with either heptyl butyrate or isobutanol and different concentrations of acetic acid in the drowning solution. Mean percentages in the same column followed by the same letter are not significantly different by Tukey's test at p < 0.05.

| [acetic acid] | heptyl butyrate | | isobutanol | |
|---|---|---|---|---|
| | V. germanica | V. pensylvanica | V. germanica | V. pensylvanica |
| 0% | 18.2 ± 4.3abc | 16.8 ± 1.9bc | 7.6 ± 1.0a | 7.1 ± 1.3a |
| .125% | 16.0 ± 4.2abc | 15.6 ± 1.7abc | 17.1 ± 1.7b | 17.0 ± 2.0b |
| .25% | 20.9 ± 3.0bc | 21.0 ± 2.1c | 19.5 ± 1.8b | 19.5 ± 1.8b |
| .50% | 29.2 ± 4.6c | 20.1 ± 1.9c | 24.8 ± 6.0b | 19.2 ± 1.3b |
| 1.0% | 8.1 ± 2.9ab | 14.6 ± 1.2ab | 17.9 ± 1.3b | 19.3 ± 1.4b |
| 2.0% | 3.7 ± 1.1a | 11.2 ± 1.6a | 19.2 ± 12.1b | 18.1 ± 1.9b |

Example 2

The following example describes experiments to evaluate further chemicals in combination with acetic acid as attractants for yellowjackets.

Materials and Methods. Trappit™ dome traps were baited with 200 ml of 0.5% acetic acid in water and 0.5 ml of a test chemical in a one ml polyethylene cap.

In the first experiment, trap treatments in caps were: an empty cap as a control, trimethylamine, 3-methyl-1-butanol, pentanol, butanol, isopropanol, 2-methyl-2-propanol, S-(−)-2-methyl-1-butanol, and isobutanol. A randomized complete block design was used with all treatments represented in each of 3 trap blocks. Traps were checked every 2–3 days and wasps were removed and traps were randomized each time traps were checked. Traps were hung on fencing or from windbreak trees at 1 to 1.5 m above ground and 5 meters apart.

In the second experiment, trap treatments were isopentyl valerate, 2-methyl-2-pentanol, 2-butanol, 2-methyl-1-pentanol, neopentyl alcohol, 3-methyl-2-butanol, 2-methyl-2-butanol, isobutanol, and 2-methyl-1-butanol. A randomized complete block design was used with all treatments represented in each of 3 trap blocks. Traps were checked every 2–3 days and wasps were removed and traps were randomized each time traps were checked. Traps were hung on windbreak trees at 1 to 1.5 m above ground and 5 meters apart.

Data were transformed to percentages of block totals and subjected to an analysis of variance (StatMost, 1995, supra).

Means were separated by Duncan's Multiple Range Test (Duncan, Biometrics Vol. 11, pages 1–41, 1955) at p<0.05.

Results. In the first experiment, greatest percentages of workers of German and western yellowjackets were captured in traps baited with isobutanol with acetic acid compared to all other treatments (Table 4). However, butanol, isopropanol, 2-methyl-2-propanol, and S-(−)-2-methyl-1-butanol were significantly attractive to both species of yellowjackets. Captures of both species in traps baited with S-(−)-2-methyl-1-butanol and acetic acid were significantly greater than in all other traps except those baited with isobutanol and acetic acid.

In the second experiment, greatest percentages of both species of yellowjackets were in traps baited with isobutanol and acetic acid and with 2-methyl-1-butanol and acetic acid (Table 5). These two treatments were not statistically different for either species. Racemic 2-methyl-1-butanol was statistically similar to isobutanol in this test for both the German and the western yellowjacket, while 2-methyl-1-pentanol was not statistically different than isobutanol. Isobutanol was significantly better as a lure for both species compared to the remainder of the treatment.

TABLE 4

Mean (±SE) percentages of wasps trapped with compounds tested with 0.5% acetic acid as attractants for german yellowjackets and western yellowjackets. First experimental series, August-September 1997, Moxee, Washington.

| Chemical | Vespula germanica | Vespula pensylvanica |
|---|---|---|
| control | 2.0 ± 0.4ab | 3.9 ± 1.0a |
| trimethylamine | 1.4 ± 0.6a | 2.1 ± 0.5a |
| 3-methyl-1-butanol | 5.7 ± 1.1abc | 6.3 ± 1.0ab |
| pentanol | 6.8 ± 1.6abc | 6.2 ± 1.3ab |
| butanol | 7.3 ± 1.1bc | 10.1 ± 1.6bc |
| isopropanol | 10.3 ± 1.6c | 8.7 ± 1.8bc |
| 2-methyl-2-propanol | 17.5 ± 1.5d | 12.2 ± 1.2c |
| S-(−)-2-methyl-1-butanol | 22.9 ± 2.6e | 23.9 ± 2.0d |
| isobutanol | 29.8 ± 3.6f | 29.3 ± 1.0e |

TABLE 5

Mean (±SE) percentages of wasps trapped with compounds tested with 0.5% acetic acid as attractants for german yellowjackets and western yellowjackets. Second experimental series, October 1997, Moxee, Washington.

| Chemical | Vespula germanica | Vespula pensylvanica |
| --- | --- | --- |
| isopentyl valerate | 0.0 ± 0.0a | 0.0 ± 0.0a |
| 2-methyl-2-pentanol | 1.9 ± 0.8a | 1.1 ± 0.8a |
| 2-butanol | 1.6 ± 1.0a | 2.7 ± 1.6a |
| 2-methyl-1-pentanol | 6.3 ± 1.6a | 12.3 ± 1.6abc |
| neopentyl alcohol | 6.3 ± 2.0a | 5.7 ± 2.3ab |
| 3-methyl-2-butanol | 8.9 ± 2.9a | 11.1 ± 4.3ab |
| 2-methyl-2-butanol | 10.8 ± 3.8a | 8.0 ± 4.1ab |
| isobutanol | 29.1 ± 9.2b | 28.6 ± 9.5c |
| 2-methyl-1-butanol | 35.1 ± 7.1b | 27.9 ± 6.6bc |

Example 3

The following example describes experiments to evaluate the efficacy of putative chemical attractants as baits for traps for social wasps. Numbers of *Polistes fiscatus* aurifer suitable for statistical analyses were captured in four of these experiments; a preliminary comparison of chemical blends, and comparisons of dosages of compounds in traps.

Chemicals were tested for attractiveness to social wasps using the Trappit™ Dome Trap (Agrisense, Fresno, Calif.). Traps were placed in orchard trees or on fences, 1.0–1.5 m above ground and 10 m apart. All experiments were conducted in Yakima County, Washington.

The first experiment evaluated wasp attraction to the combination of isobutanol and acetic acid and the combination of butyl butyrate and acetic acid. Heptyl butyrate was included in the series as a positive comparison because of its attractiveness to species of Vespula (Davis et al. 1969, supra). Seven treatments (trap baits) were compared in this experiment: isobutanol, isobutanol and acetic acid, butyl butyrate, butyl butyrate and acetic acid, heptyl butyrate, heptyl butyrate and acetic acid, and an unbaited trap as a control. Isobutanol, butyl butyrate, and heptyl butyrate were loaded into polyethylene caps at a dose of 1 ml and caps were pinned to the inside top of the trap. Acetic acid was placed in a drowning solution within the trap, at 0.5% of 200 ml. A randomized complete block design was used, with 3 block replicates. Traps were checked and randomized 3 times per week for 2 weeks. Trap catch data for blocks in which paper wasps were captured were transformed to percentages of block totals and subjected to an analysis of variance. Treatment means were separated using Tukey's test at p<0.05.

The second and third tests were comparisons of dosages of isobutanol in polyethylene caps, with a 0.5% solution of acetic acid in the trap drowning solution. This was conducted both with a high dosage series and a low dosage series. The high dosage series of baits consisted of 0, 12.5%, 25%, 50%, 75%, and 100% isobutanol in mineral oil as an extender, with one ml of the mixture placed in a cap. The low dosage series of baits consisted of 0, 1%, 2%, 4%, 8%, and 16% isobutanol in mineral oil as an extender, with one ml of the mixture placed in a cap. For each experiment, a randomized complete block design was used, with 6 sets of traps set up. Traps were checked every 2–3 days for 10 days, providing 18 replicates per treatment. The high dosage test was set up Aug. 8, 1997 and the low dosage test was set up Aug. 26, 1997. Trap catch data for blocks in which golden paper wasps were captured (14 of 18 data sets for each experiment) were transformed to percentages of block totals for regression analyses.

The fourth test compared the attractiveness of different concentrations of acetic acid in the drowning solution; 0, 0.125, 0.25, 0.5, 1, and 2%. All traps were also baited with a cap containing one ml of 16% isobutanol in mineral oil. A randomized complete block design was used, with 6 sets of traps set up on Sep. 2, 1997. Traps were checked every 2–3 days for 1 week providing 18 block replicates. Trap catch data for blocks in which wasps were captured (8 of 18) were transformed to percentages of block totals for regression analysis.

Results.

Figure 2:
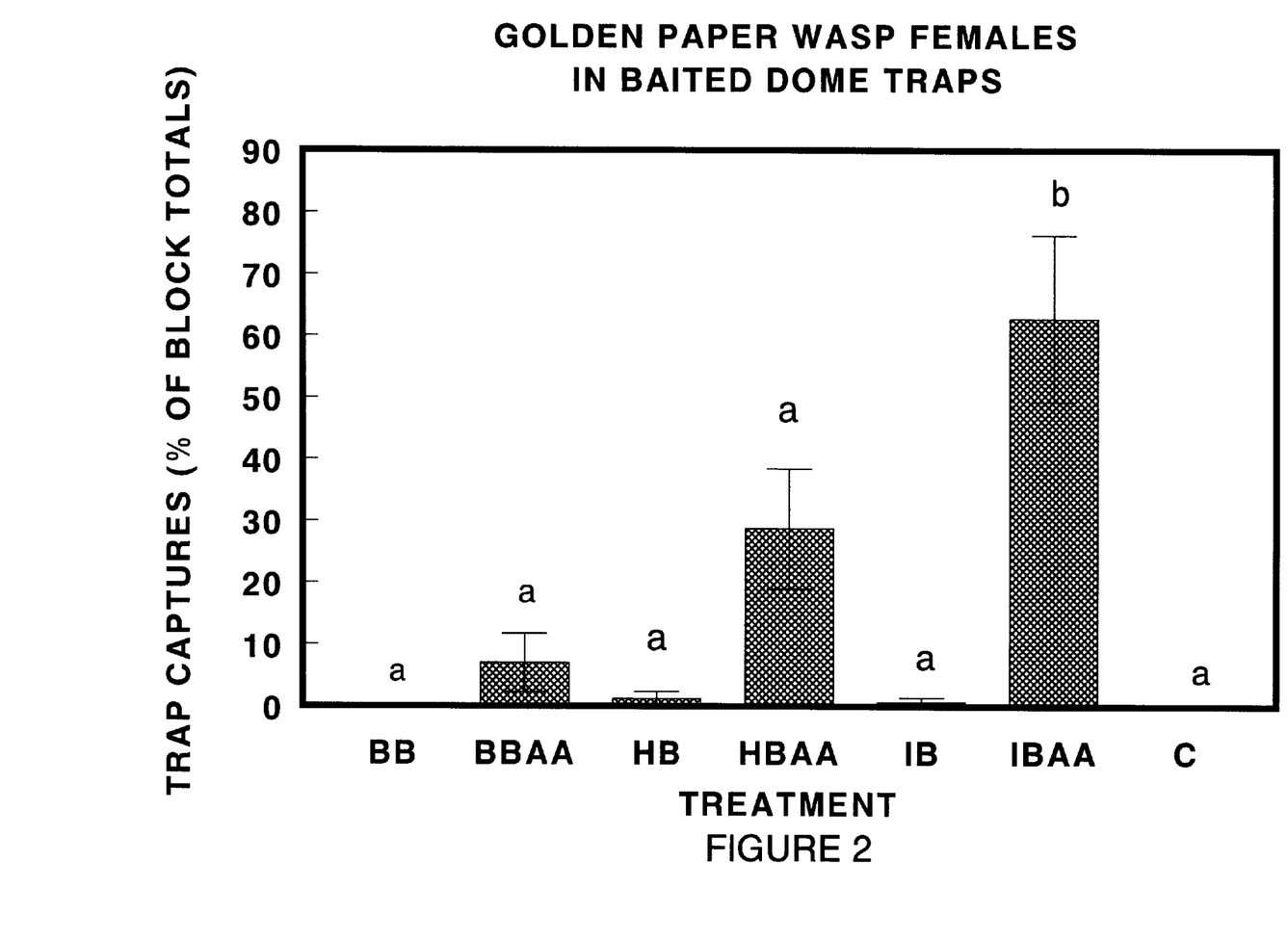
FIG. 2 shows the percentages of female *P. fuscatus aunifer* captured in traps baited with attractant blends. Bars with the same letter are not significantly different by Tukey's test at 0<0.05.

Comparison of chemical blends. Nineteen male and 72 female golden paper wasps were captured in this experiment. Males captured with different baits were not significantly different. Females were captured in significant numbers in traps baited with the combination of isobutanol and acetic acid (FIG. 2).

Figure 3A:
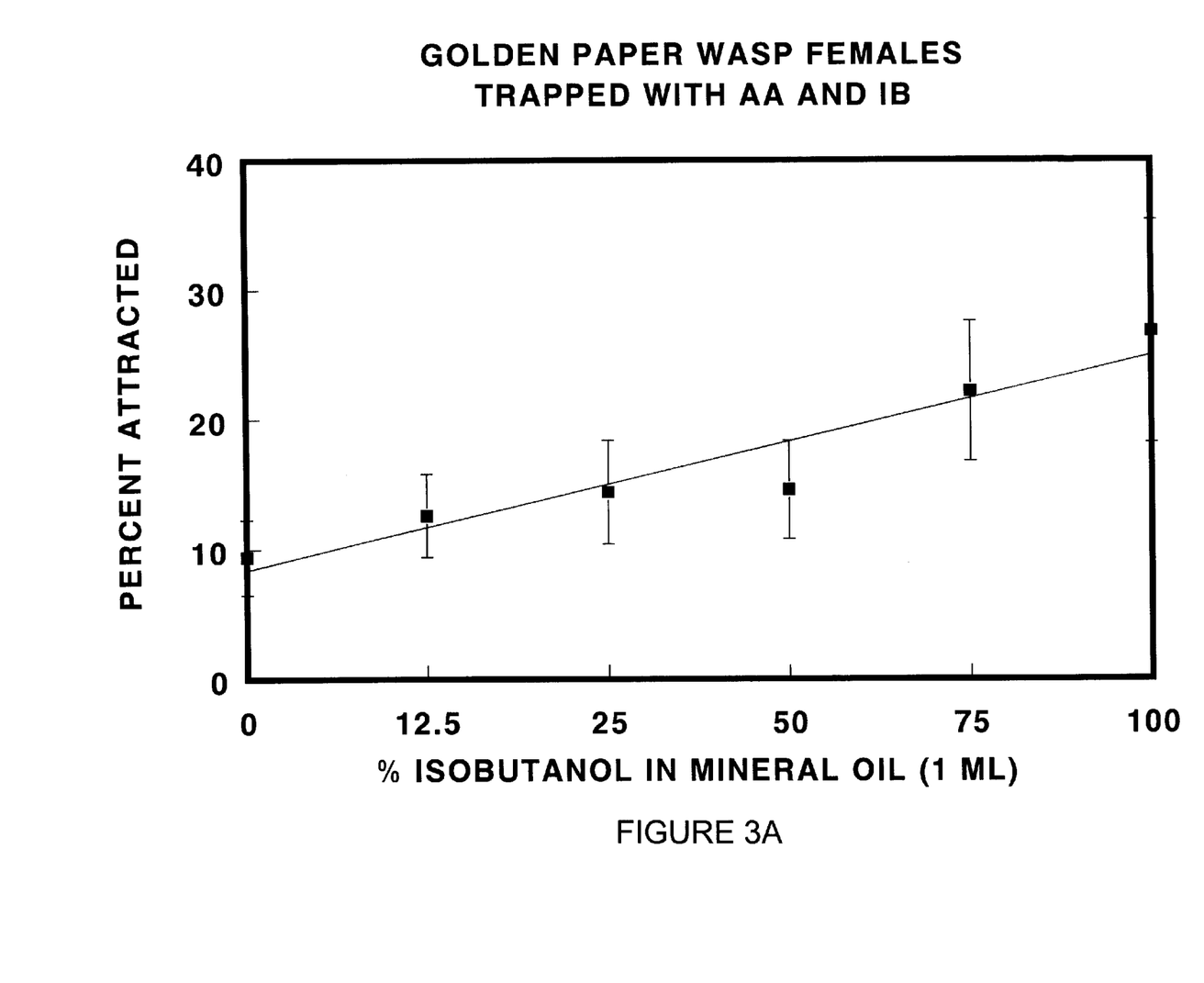
FIG. 3A shows a high dosage series of baits having 0, 12.5%, 25%, 50%, 75%, and 100% isobutanol in mineral oil as an extender, with one ml of the mixture placed in a cap.
Figure 3B:
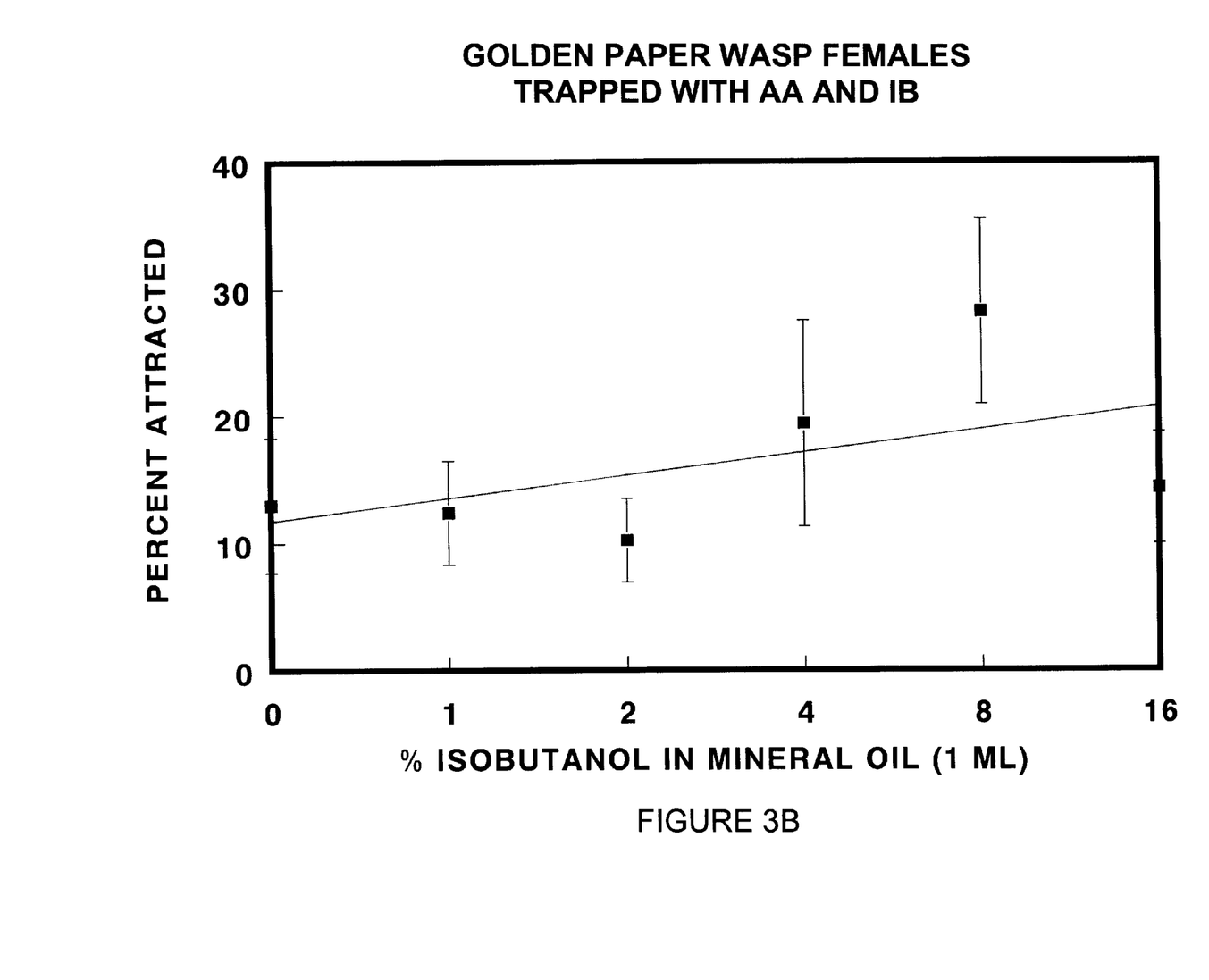
FIG. 3B shows a low dosage series of baits having 0, 1%, 2%, 4%, 8%, and 16% isobutanol in mineral oil as an extender, with one ml of the mixture placed in a cap.

Comparison of dosages of isobutanol. In the high dosage series, 19 males and 198 females were captured. Percentages of females captured in traps were significantly related to isobutanol dosage ($r^2$=0.92, T=4.68, df=4, p=0.0095), with the greatest percentage captured in the highest dosage tested (FIG. 3A). Sixty three males and 101 females were captured in the isobutanol low dosage series. In the low dosage series, percentages of females captured were not significantly related to isobutanol dosage ($r^2$ =0.21, T=0.44, df=4, p=0.68). (FIG. 3B). Percentages of males captured were not significantly related to isobutanol dose for either the high dosage series or the low dosage series.

Comparison of acetic acid concentrations. Thirty seven males and 72 females were captured in this test. Percentages of males and females captured were not significantly related to acetic acid concentration ($r^2$=0.22, T=0.7, df=4, p=0.52 for females).

This blend is the first demonstrated chemical attractant for attracting and trapping a species of paper wasp (Polistes).

It is understood that the foregoing detailed description is given merely by way of illustration and that modification and variations may be made within, without departing from the spirit and scope of the invention.

What is claimed is:

1. A method for attracting yellowjacket wasps or paper wasps, which comprises placing in an area where wasps are to be attracted a dispenser means which provides an effective attractant amount of a vapor blend of vapor of (I) acetic acid and vapor of (II) one or more compounds selected from the group consisting of isobutanol, racemic 2-methyl-1-butanol, S-(−)-2-methyl-1-butanol, 2-methyl-2-propanol, heptyl butyrate, and butyl butyrate.

2. The method of claim 1 wherein said vapor blend is provided by a dispenser means which contains a mixture of (I) acetic acid and (II) one or more compounds selected from the group consisting of isobutanol, racemic 2-methyl-1-butanol, S-(−)-2-methyl-1-butanol, 2-methyl-2-propanol, heptyl butyrate, and butyl butyrate.

3. The method of claim 1 wherein said vapor blend is provided by a dispenser means which comprises a first dispenser which contains (I) acetic acid and a second dispenser which contains (II) one or more compounds selected from the group consisting of isobutanol, racemic 2-methyl-1-butanol, S-(−)-2-methyl-1-butanol, 2-methyl-2-propanol, heptyl butyrate, and butyl butyrate, wherein said first and second dispensers are in proximity effective to provide said vapor blend of I and II.

4. The method of claim 1 wherein said dispenser means contains 2-methylpropyl acetate and said vapor blend comprises vapors of acetic acid and isobutanol.

5. The method of claim 1 wherein said acetic acid vapor in said vapor blend is provided by aqueous acetic acid, concentrated acetic acid or ammonium acetate.

6. The method of claim 1 wherein said attracted yellowjacket wasps or paper wasps are trapped within a trapping means for yellowjacket wasps or paper wasps which includes said dispenser means.

7. The method of claim 1 which further includes a means for controlling yellowjacket wasps or paper wasps.

8. An attractant composition for yellowjackets or paper wasps, which consists essentially of a vapor blend of vapor of (I) acetic acid and vapor of (II) heptyl butyrate, butyl butyrate or mixtures therof, wherein said composition provides an effective yellowjacket or paper wasp attractant amount of said vapor blend of I and II.

9. The composition of claim 8 wherein said vapor of acetic acid is provided by aqueous acetic acid, concentrated acetic acid, or ammonium acetate.

10. The composition of claim 8 wherein said effective attractant amount of said vapor blend is provided by a dispenser means which contains a mixture I and II.

11. The composition of claim 8 wherein said effective attractant amount of said vapor blend is provided by a dispenser means comprising a first dispenser which contains I and a second dispenser which contains II, wherein said first and second dispensers are in sufficient proximity to provide said vapor blend of I and II.

12. The composition of claim 8 in combination with a trapping means for yellowjacket wasps or paper wasps.

13. A method for attracting yellowjacket wasps or paper wasps, which comprises providing two volatile components in sufficient proximity to one another to form a volatilized mixture thereof in a surrounding atmosphere, wherein one component is acetic acid and the other component is one or more compounds selected from the group consisting of isobutanol, racemic 2-methyl-1-butanol, S-(−)-2-methyl-1-butanol, 2-methyl-2-propanol, heptyl butyrate, and butyl butyrate.

14. A kit for attracting yellowjacket wasps or paper wasps, which comprises two components, wherein one component is acetic acid and the other component is heptyl butyrate.

15. A packaged attractant comprising two components, wherein one component is acetic acid and the other component is heptyl butyrate, wherein said components are packaged in separate containers and wherein said packaged attractant further comprises instructions for producing a volatilized blend of said two components when said components are released from said containers.

16. An attractant composition for yellowjackets or paper wasps, which comprises a vapor blend of vapor of (I) acetic acid and vapor of (II) heptyl butyrate, wherein said composition provides an effective yellowjacket or paper wasp attractant amount of said vapor blend of I or II.

17. An attractant composition for yellowjackets or paper wasps, which consists of a vapor blend of vapor of (I) acetic acid and vapor of (II) one or more compounds selected from the group consisting of isobutanol, racemic 2-methyl-1-butanol, S-(−)-2-methyl-1-butanol, 2-methyl-2-propanol, heptyl butyrate, and butyl butyrate, wherein said composition provides an effective yellowjacket or paper wasp attractant amount of said vapor blend of I and II.

18. An attractant composition for yellowjackets or paper wasps, which consists of a vapor blend of vapor of (I) acetic acid and vapor of (II) one or more compounds selected from the group consisting of isobutanol, racemic 2-methyl-1-butanol, S-(−)-2-methyl-1-butanol, 2-methyl-2-propanol, heptyl butyrate, and butyl butyrate, wherein said composition provides an effective yellowjacket or paper wasp attractant amount of said vapor blend of I and II, and wherein said composition further includes a means for controlling yellowjackets or paper wasps.

\* \* \* \* \*